(12) United States Patent
Daft et al.

(10) Patent No.: US 7,006,955 B2
(45) Date of Patent: Feb. 28, 2006

(54) SYSTEM AND METHOD FOR STATISTICAL DESIGN OF ULTRASOUND PROBE AND IMAGING SYSTEM

(75) Inventors: Christopher M. W. Daft, Clifton Park, NY (US); William Macomber Leue, Albany, NY (US)

(73) Assignee: General Electric Company, Niskayuna, NY (US)

(*) Notice: Subject to any disclaimer, the term of this patent is extended or adjusted under 35 U.S.C. 154(b) by 797 days.

(21) Appl. No.: 09/976,582

(22) Filed: Oct. 15, 2001

(65) Prior Publication Data

US 2003/0154062 A1   Aug. 14, 2003

(51) Int. Cl.
G06F 7/48 (2006.01)
(52) U.S. Cl. .................. 703/5; 600/443; 600/437; 382/128
(58) Field of Classification Search .............. 703/5; 600/458, 443, 459, 437; 604/85; 382/128; 715/751

See application file for complete search history.

(56) References Cited

U.S. PATENT DOCUMENTS

| | | | | |
|---|---|---|---|---|
| 5,919,138 | A * | 7/1999 | Ustuner ............... | 600/443 |
| 6,200,267 | B1 * | 3/2001 | Burke ................. | 600/443 |
| 6,595,921 | B1 * | 7/2003 | Urbano et al. ........ | 600/437 |
| 6,621,917 | B1 * | 9/2003 | Vilser ................ | 382/128 |
| 6,623,430 | B1 * | 9/2003 | Slayton et al. ....... | 600/439 |
| 6,626,831 | B1 * | 9/2003 | Holley et al. ........ | 600/437 |
| 6,674,879 | B1 * | 1/2004 | Weisman et al. ...... | 382/128 |
| 6,692,439 | B1 * | 2/2004 | Walker et al. ........ | 600/443 |
| 6,741,265 | B1 * | 5/2004 | Ghosh et al. ......... | 715/751 |
| 6,751,490 | B1 * | 6/2004 | Esenaliev et al. ..... | 600/310 |
| 2001/0056236 | A1 * | 12/2001 | Angelsen ............. | 600/458 |
| 2001/0056256 | A1 * | 12/2001 | Hughes et al. ........ | 604/85 |
| 2002/0012289 | A1 * | 1/2002 | Gilbert et al. ....... | 367/135 |
| 2002/0012999 | A1 * | 1/2002 | Madsen et al. ........ | 436/8 |
| 2002/0042577 | A1 * | 4/2002 | Hatangadi et al. ..... | 600/459 |
| 2002/0050169 | A1 * | 5/2002 | Ritter et al. ........ | 73/606 |
| 2002/0135273 | A1 * | 9/2002 | Mauchamp et al. ...... | 310/334 |
| 2003/0032884 | A1 * | 2/2003 | Smith et al. ......... | 600/459 |

OTHER PUBLICATIONS

Sredni, "Design of experiments: A tool for continuous process improvement", IEEE 1992.*

Frank, "The use of experimental design techniques in simulation", ACM 1968.*

(Continued)

Primary Examiner—Paul L. Rodriguez
Assistant Examiner—Kandasamy Thangavelu
(74) Attorney, Agent, or Firm—Fletcher Yoder

(57) ABSTRACT

A system and method for statistical design of an ultrasound probe and imager system, and an associated graphical user interface for selecting input parameters to be used in an ultrasound simulation. The process and computer code allow the performance of a probe and imager combination to be specified and jointly optimized in image quality terms. The designs produced optimize both the image quality and other CTQ (critical to quality) parameters, such as the distribution of regulatory power indices and mechanical index. These CTQs indirectly affect image quality through their effect on patient dose. The Transducer Design Advisor incorporates a graphical user interface for facilitating selection of a parameter set to be used in the simulation. The user selects a desired parameter set by navigating across and interacting with a succession of windows. The user specifies various geometric characteristics of the transducer and how the user wants to simulate the imager system. Finally, the user specifies weights for the various CTQs at different depths. Based on these inputs, the Transducer Design Advisor creates the files needed by the ultrasound simulator.

37 Claims, 11 Drawing Sheets

OTHER PUBLICATIONS

McKeighen, "Optimization of Broadband Transducer Designs by Use of Statistical Design of Experiments", IEEE Trans. Ultrasonics, Ferroelec. and Freq. Control, vol. 43, No. 1, pp. 63-70 (1996).

Selfridge et al., KLM Transducer Model Implementation Using Transfer Matrices, Proc. IEEE Ultrasonics Symposium, San Francisco, 1985.

Jensen et al., Computer Phantoms for Simulating Ultrasound B-mode and cmf Images. 23rd Acoustical Imaging Symposium, Boston, Apr. 13-16, 1997.

Myers et al. Response Surface Methodology: Process and Product in Optimization Using Designed Experiments, Chap. 6, Wiley, (1995).

* cited by examiner

QUESTION: SPECIFY THE RELATIVE CTQ WEIGHTS OVER RANGE

ANSWER:

CTQ TO EDIT: ElevSLE

RANGE STEP: 10

BACK | GO TO | NEXT

FINISH | | ?

FIG. 11

SYSTEM AND METHOD FOR STATISTICAL DESIGN OF ULTRASOUND PROBE AND IMAGING SYSTEM

BACKGROUND OF THE INVENTION

This invention generally relates to ultrasound imaging systems. In particular, the invention relates to the design of ultrasound transducer probes for use in an ultrasound imaging system.

Designing the probe in an ultrasound imager is a difficult task because of the large number of factors involved. A typical probe comprises several layers whose dimensions determine its mechanical and electrical behavior. Prior art [see, e.g., R. E. McKeighen, "Optimization of Broadband Transducer Designs by Use of Statistical Design of Experiments," IEEE Trans. Ultrasonics, Ferroelectrics and Frequency Control, Vol. 43, No. 1, pp. 63–70 (1996)] has described statistical means to seek optimal behavior of the impulse response of the device. However, this work neglects the increasingly significant coupling between the imager parameters and the probe design. Particularly when the aperture is divided into several rows in the slice thickness [elevation] dimension, such as in active matrix arrays, the image quality consequences of such coupling becomes acute. The business requirement is for a jointly optimal probe and image-parameter design, in which the variability of image quality (image quality) is minimally impacted by manufacturing tolerances. These tolerances strongly influence the production costs. A comprehensive method for achieving these objectives is needed.

The matching of a new prototype probe to a given ultrasound imager is highly resource-intensive. Typically, an engineer manually varies parameters such as the F-numbers for each focal zone and receive depth, in order to improve image quality parameters such as image uniformity, detail and contrast resolution, etc. One way to increase an imager's value to the customer is by providing preset parameter sets with which the physician can rapidly set the machine up for a given examination. To maximize the image quality potential, a modern imager may have several thousand parameters affecting each preset. There is a need for a process of choosing these parameters that can be at least partially automated for new probes. This process should also allow more mundane tasks, such as the porting of a probe to a new platform, to be completely automated. Several months of time-to-market advantage can be realized using such a method, as well as an improvement in engineering productivity.

SUMMARY OF THE INVENTION

The present invention comprises a process and a computer system that allow the performance of a probe and imager combination to be specified and jointly optimized in image quality terms. The designs produced optimize both the image quality and other CTQ (critical to quality) parameters, such as the distribution of regulatory power indices and mechanical index. These CTQs indirectly affect image quality through their effect on patient dose.

The computer system in accordance with the preferred embodiment of the invention has the following features and capabilities:

(1) The ability to capture and model not just a few design parameters of an ultrasound transducer, but hundreds of them, and not just "best guess" values, but actual values taken from the databases of real probes that are in daily use.

(2) The ability to model the behavior of a transducer design in a complete system context, including details such as the aperture opening schedule, number of available system channels, number of focal zones, their depths, and the depths at which data from multiple zones is to be spliced together; as opposed to modeling only the transducer in isolation.

(3) The ability to integrate the one-dimensional acoustic stack design (KLM model) with the full system model, and to allow acoustic stack parameters (e.g., number of matching layers, their thicknesses and material properties) to be simultaneously optimized along with system-related properties (e.g., focal zone depths, F numbers) in a single DOE (design of experiment) run. Traditionally, the acoustic stack is optimized using CTQ parameters such as bandwidth and sensitivity, and then the optimization of the aperture and lens is done separately.

(4) The ability to do true statistical design, as opposed to "point" design. That is, being able to simulate the statistical distribution of quality measures (CTQs) and to calculate their sensitivity to variations in design parameters. This ability allows one to create "robust designs" which are not only optimized, but are resistant to performance degradation caused by manufacturing variation.

The invention further comprises a method and computer system for choosing imaging parameters to be included in preset parameter sets for new transducer probes.

In addition, the invention is directed to a Transducer Design Advisor comprising a graphical user interface for facilitating selection of a parameter set to be used in a simulation. The user selects a desired parameter set by navigating across and interacting with a succession of windows. The user specifies various geometric characteristics of the transducer and how the user wants to simulate the imager system. Finally, the user specifies weights for the various CTQs at different depths. Based on these inputs, the Transducer Design Advisor creates the files needed by the ultrasound simulator.

The invention further comprises a method for speeding up the probe design process via a comprehensive simulation and an intelligent "wizard".

The invention also comprises an automated method for optimizing transducer geometry and imager parameters based on a cost function that is a linear combination of range-dependent CTQs.

In accordance with one preferred embodiment of the invention, the first stage of the design method comprises several computational blocks, several databases, and an image quality specification. The functional blocks comprise: (a) a Transducer Design Advisor to guide the creation of a parameter set; (b) an acoustic stack simulator which computes an impulse response given a specification of the layers in the probe; (c) an ultrasound beam simulator which computes acoustic diffraction given an impulse response and a definition of the aperture geometry; (d) a "scoring" package that quantifies the diagnostic value of the image simulated; and (e) a controller for controlling the simulations in accordance with a statistical design of experiment (DOE). The databases comprise a repository of material properties, including those materials suited to piezoelectric energy conversion, acoustic impedance matching, backing and focusing of acoustic beams; and an imager parameter database, containing data such as the apodization functions, focusing schedule and F-numbers for a given probe.

In accordance with the preferred embodiment, the inputs to the process are an image quality specification and some selected parameters to optimize. These parameters are chosen via the Transducer Design Advisor. The Transducer Design Advisor allows the designer to select which of the controllable parameters will be varied, and which are held constant during the various simulation runs. These controllable parameters are DOE variables. The Transducer Design Advisor also guides the selection of a suitable phantom for the simulation. A phantom is a virtual object whose function is to simulate a patient or other target for ultrasound energy. It contains simulated features of varying size, shape, location, and density of acoustic scatterers. A typical phantom might contain hyper-echoic features of small size whose purpose is to allow an assessment of the performance of the ultrasound imaging system for detecting small-objects, and also hypo-echoic features to allow an assessment of system performance in detecting low-density objects. A different phantom might provide a somewhat realistic model of a part of human anatomy.

The DOE controller varies the DOE variables in a designed experiment whose character and resolution are chosen by a DOE advisor. The DOE advisor is a small expert system that chooses the type of designed experiment appropriate for the case under study. Designed experiments allow all of the DOE variables to vary simultaneously to capture their effects on the image quality metrics, with an optimally small number of simulation runs.

In accordance with the preferred embodiment of the invention, the DOE variables and accompanying fixed parameters are presented to the acoustic stack simulator, which computes an impulse response for the current probe specification. That impulse response, together with the phantom and imager parameters, forms the input to the beam simulator. The beam simulator generates an image; it computes the diffraction of the sound from the aperture to the scatterer locations, the scattering itself, and the diffraction back to the aperture. This image can be reviewed visually (for example, on the display monitor of the user's PC) for artifacts.

For the purpose of making transfer functions, the customer value of the image is scored, based on the image quality specification. The outputs of this process are transfer functions relating each DOE variable to each image quality metric, and the DOE variables to the overall image quality. The business value of these transfer functions is threefold. First, plots of the transfer functions will aid a skilled probe designer. Second, the partial derivatives show the sensitivity of the design to manufacturing variability. Third, the transfer functions can be used to optimize the performance and robustness of the design.

The advantages of the foregoing method are manifold.

First, probe parameters, such as layer thickness and material properties, are optimized jointly with imager parameters, such as F-numbers and focusing schedules. The advent of multi-row probes has rendered the standard practice of addressing the probe and system parameters separately wholly inadequate. This is due to the strong coupling between the two classes of parameters.

Second, deriving transfer functions explicitly has great advantages over standard design practice (evaluating the point-spread function of the imager at several values, and judging the behavior of the probe manually). Typically, the input variables are varied one at a time, which again ignores coupling of parameters. Also, a realistic number of simulations requires scanty coverage of the design space. The transfer function approach extracts the maximum information from a given computational budget, and makes sophisticated optimization techniques feasible.

Third, often the variability of image quality is almost as important as reaching a globally optimal image quality. With this method it is easy to use a program to gauge the effect of variability in system gain (due to factors such as temperature changes and/or component tolerance) and probe material properties and layer thickness variability on image quality. To do this with standard design methods requires an impractical amount of computation.

Fourth, the final result shows performance and its variance as a function of cost, which can inform the best possible management decision on product positioning.

BRIEF DESCRIPTION OF THE DRAWINGS

FIG. 11 is a schematic depicting a window of the Transducer Design Advisor for implementing a "policy" in accordance with the preferred embodiment of the invention. This policy specification is a list of the importance of each CTQ as a function of range. The meaning of the term "policy" will be defined in more detail below.

DETAILED DESCRIPTION OF THE PREFERRED EMBODIMENTS

The first stage of the design method in accordance with the preferred embodiment of the invention comprises several computational blocks, several databases, and an image quality specification (typically generated by Systems Engineering).

Figure 1:
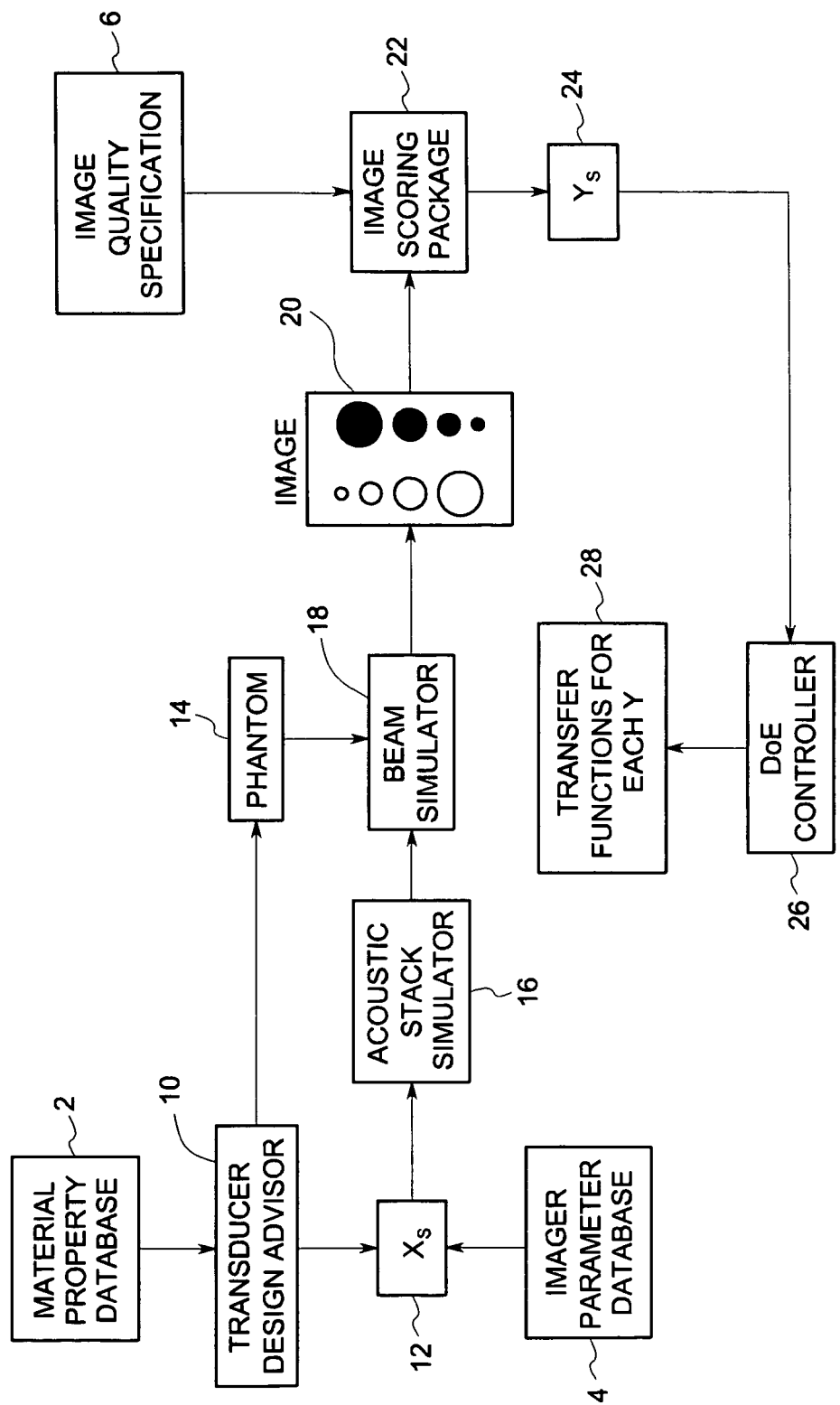
FIG. 1 is a flowchart showing the overall information flow for statistical design of a probe and an imager in accordance with the preferred embodiment of the invention.

Block 10 in FIG. 1 represents the Transducer Design Advisor (TDA) for guiding creation of a parameter set in accordance with the preferred embodiment. The Transducer Design Advisor is used to specify some of the characteristics of a probe, including material properties retrieved from a material properties database 2. The material properties data in database 2 includes, but is not limited to, the properties of those materials suited to piezoelectric energy conversion, acoustic impedance matching, backing and focusing of acoustic beams. Further, the Transducer Design Advisor allows the designer to select which of the controllable parameters will be varied, and which are held constant during the various simulation runs. These controllable parameters, which are DOE variables, will be referred to as "x's" (item 12 in FIG. 1). The Transducer Design Advisor also guides the selection of a suitable phantom for the simulation (item 14 in FIG. 1).

In accordance with the preferred embodiment of the invention, the x's and accompanying fixed parameters are presented to the acoustic stack simulator 16, which computes an impulse response for the current probe specification. Preferably, the acoustic stack simulator is of the type described by Selfridge and Gehlbach in "KLM Transducer Model Implementation Using Transfer Matrices," Proc. IEEE Ultrasonics Symposium, San Francisco (1985)], or is a finite element model.

The impulse response from the acoustic stack simulator, together with the phantom and imager parameters, forms the input to the ultrasound beam simulator 18. Some of the imager parameters are defined in the Transducer Design Advisor 10; some are varied during the DOE runs, while others are copied from the values for similar imaging situations, which are available in the database 4 of previously optimized probes. Dividing the parameters in this fashion is necessary because the total set of x's usually exceeds 1000. A practical number of x's is less than 20, if the simulation is run on a single processor system of low cost. The imager parameter database 4 contains data such as the apodization functions, focusing schedule and F-numbers for a given probe.

Preferably, the ultrasound beam simulator 18 computes acoustic diffraction given an impulse response and a definition of the aperture geometry. The preferred ultrasound beam simulator is based on the FIELD II program [see Jørgen Arendt Jensen and Peter Munk, Computer Phantoms for Simulating Ultrasound B-Mode and CFM Images," 23rd Acoustical Imaging Symposium, Boston, Mass., Apr. 13–16 (1997)]. A finite element code may also be used for the beam simulator, in order to simulate nonlinear sound propagation and scattering. The beam simulator output can be displayed as an image 20.

The method in accordance with the preferred embodiment further comprises a "scoring" package 22 that quantifies the diagnostic value of the image simulated. The inputs to the process are an image quality specification 6 and the parameters chosen via the Transducer Design Advisor for optimization. The image quality specification 6 may include the following: detail resolution requirements; contrast resolution requirements; measures of the variance of the detail and contrast resolutions over the range of interest in the image; sidelobe level requirements; measures of the importance of a smoothly varying gain of the imager and probe with range; acoustic power performance; and imager parameters, like its preamplifier input impedance, noise level and temperature drift.

In accordance with the preferred embodiment, the resolution and sidelobe requirements are specified both for azimuth (conventionally, the imaging dimension) and elevation (the slice thickness direction). The systems engineer quantifies the importance of these (or other) image quality metrics with numeric values that usually vary with range. These will be referred to in this disclosure as "Y's". As previously discussed, the Transducer Design Advisor 10 is used to specify some of the characteristics of a probe to meet the requirements.

In accordance with the preferred embodiment of the invention, a controller 26 is provided for performing a statistically designed simulation. The DOE controller 26 varies the x's in a designed experiment whose character and resolution are chosen by a DOE advisor (a user interface "wizard" similar in functionality to the Transducer Design Advisor and forming part of the DOE controller 26). The DOE advisor is a small expert system that chooses the type of designed experiment appropriate for the case under study. Designed experiments allow all of the x's to vary simultaneously to capture their effects on the image quality Y's, with an optimally small number of simulation runs.

The beam simulator generates an image; it computes the diffraction of the sound from the aperture to the scatterer locations, the scattering itself, and the diffraction back to the aperture. This image 20 can be reviewed visually (for example, on the display monitor of the user's PC) for artifacts. For the purpose of making transfer functions, the customer value of the image is scored, based on the image quality specification:

$$Y = \sum_{i=1}^{M} \sum_{j=1}^{N} c_i(r_j) y_i(r_j)$$

where $y_i$ is the i-th of M image quality parameters, $r_j$ is the j-th of N ranges in the image, and $c_i$ is a range-dependent value coefficient for the i-th image quality parameter. The $c_i(r_j)$ form the image quality specification 6 mentioned earlier. The Y's are indicated by block 24 in FIG. 1.

The $y_i$ are normalized with respect to a "nominal" design. They therefore represent the percentage improvement or degradation of a certain DOE parameter set. The coefficients in the image quality specification can therefore be viewed as answering the question: "How much does the user care about a 1 percentage point improvement in this CTQ, compared to a similar improvement in other CTQs?"

The DOE controller 26 comprises a regression tool which generates transfer functions (step 28 in FIG. 1) from the simulation-based data. The DOE controller can automatically import the DOE data and produce Y=f(x). The DOE controller further comprises a transfer function tool which imports the generated transfer functions and represents them numerically in a spreadsheet. The transfer function tool will also generate diagnostic data (such as correlations and sensitivities) and three-dimensional visualization.

The transfer functions relate each x to each y, and the x's to the overall image quality, denoted by Y:

$$y_i = f_i(x_1, x_2, x_3, \ldots x_L)$$

$$Y = F(x_1, x_2, x_3, \ldots x_L)$$

The business value of these transfer functions is threefold:

First, plots of the transfer functions will aid a skilled probe designer. The effect of each of the $x_k$ on the parameters of the image CTQs $y_i$ and the overall performance Y can be quickly visualized through main effects plots. This builds intuition in an uncertain environment. The quantitative effect of each tradeoff is made plain.

Second, the partial derivatives $$\frac{\partial y_i}{\partial x_k} \text{ and } \frac{\partial Y}{\partial x_k}$$

show the sensitivity of the design to manufacturing variability. The computation of transfer functions provides a far more complete picture than was previously available using the standard design practice of "point" performance evaluations.

Figure 2:
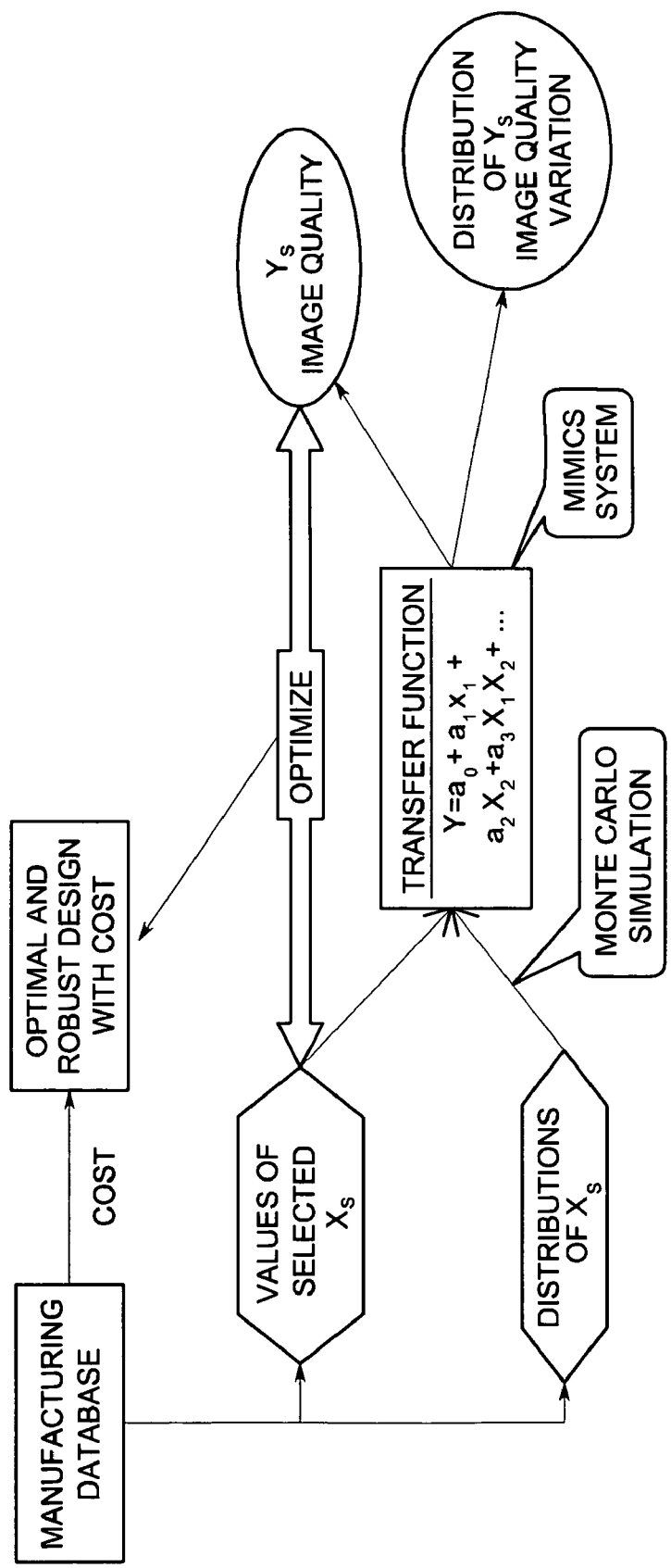
FIG. 2 is a flowchart detailing the usage of transfer functions (derived using the method shown in FIG. 1) in predicting an optimal and robust design.

Third, the transfer functions can be used to optimize the performance and robustness of the design. Details of this are shown in FIG. 2.

Figure 3:
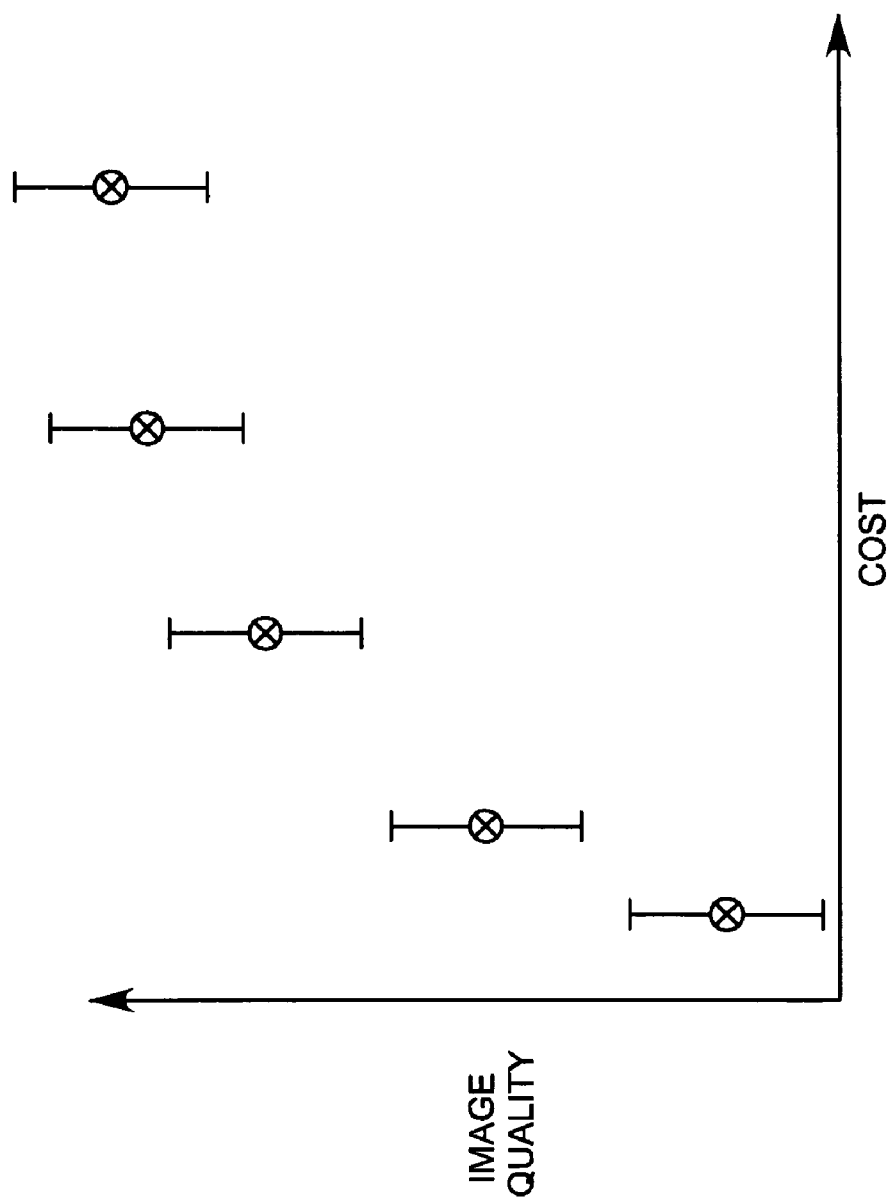
FIG. 3 is a representative graph of image quality (mean and variance) as a function of cost as determined by the statistical design in accordance with the preferred embodiment of the invention.

Since transfer functions can be evaluated with many orders of magnitude less resources than the imager simulation, the optimization of the imager parameters can proceed with large numbers of x's and Y's, at modest computational cost. FIG. 2 shows how to optimize both the image quality ($y_i$ and Y) and the variance of these parameters. The variances of the x's are specified by the manufacturing database for each x, together with the cost associated with each tolerance level. The output of this process will look as is shown in FIG. 3. This final output of the statistical design method enables a data-driven decision on product positioning in the marketplace. This graph is the precise distillation of information needed to optimally target the product. For each cost, an image quality measure has been computed, which is the best available under the cost constraints. The image quality measure directly was determined from Systems Engineering's specification of the probe. The error bars show the variation in image quality given the tolerances available at that cost.

Figure 4:
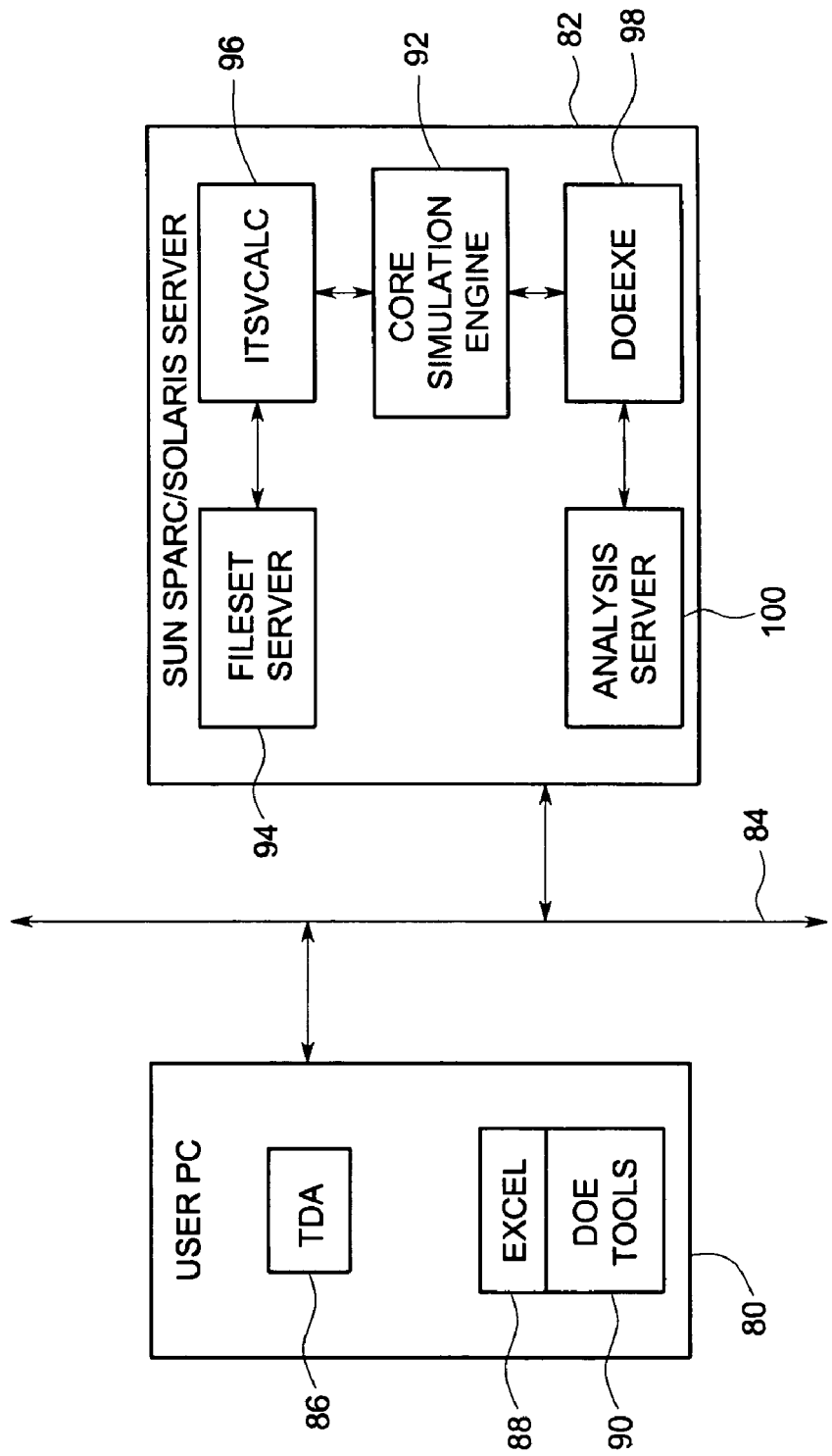
FIG. 4 is a block diagram showing a computer system for statistical design of a probe and an imager in accordance with the preferred embodiment of the invention.

In accordance with the preferred embodiment, the software components are distributed between a user's PC 80 and a remote server 82, as shown in FIG. 4, PC 80 and server 82 being connected via a network 84, e.g., a local area network or wide area network. The remote server may be implemented as a Sun Sparc/Solaris server. The Transducer Design Advisor (TDA) software 86, the Microsoft Excel program 88 and various DOE software tools 90 reside on the user's PC 80. The DOE tools 90 are incorporated as extensions to the Excel program. The remote server 82 comprises the following software components: a core simulation engine 92; a FilesetServer program 94 which handles transactions between the Transducer Design Advisor 86 and the remote server software; an itsucalc program 96 which runs a single (non-DOE) simulation specified by a master parameters file (*.EXIC) and returns a binary results file (*.SIMD) containing either contour maps or an image, depending on command line options; a doeexe program 98 which runs simulations in the DOE mode (most of the code is common between itsucalc and doeexe; only the outer layers differ); and an analysis server 100, which is a computer program that facilitates analysis integration by providing communication links between the simulator and Excel, i.e., the analysis server translates standard Set, Get and Execute commands coming from Excel into a language that the simulator can understand. As used hereinafter, the term "simulator" refers to the doeexe program 98 in conjunction with the core simulation engine 92.

In addition to creating the files that define a DOE analysis, the Transducer Design Advisor also has some auxiliary functions to make the user's life easier. First, the Transducer Design Advisor will copy all of the files for an analysis over to the remote host that the user wants to run the simulation on, make the necessary edits to these files for the particular file system that the remote host has, and install them in the right directories for access by the DOE tools 90 and the analysis server 100. Second, the Transducer Design Advisor will also let the user run a simulation with a specific set of parameters, and then present the results in a variety of graphical formats. Performing single runs is a good way to let the user gain insight into behavior of the simulator, and the graphical output presents a wealth of information that is not captured in its entirety in the CTQs. Third, the Transducer Design Advisor will run a simulation which includes a simple "patient" model and display the resulting image. The user can directly see sidelobes, speckle pattern, and other image features that are marks of image quality. Seeing an image can sometimes be easier and more direct than just looking at numeric CTQs.

All of the auxiliary functions for the Transducer Design Advisor 86 are implemented as the client half of a client-server pair, with the server functions being implemented on the remote host 82 by the FilesetServer process 94. This is the server process that a Transducer Design Advisor client connects to for the purposes of: (a) uploading a simulation fileset to a server; (b) uploading a phantom specification file to a server; and (c) performing a single (non-DOE) simulation run. The server-side software components are capable of handling any number of simultaneous client connections, but for the sake of simplicity, this disclosure will only discuss the example of a single client. The FilesetServer program 94 preferably resides on the remote server 92 and is written in Java 2 in the preferred embodiment. The main network protocol used between the Transducer Design Advisor 86 and the FilesetServer program 94 is TCP/IP.

In accordance with the preferred embodiment of the invention, the Transducer Design Advisor 86 is a Java application which helps create and modify the files needed to use an ultrasound simulator with a Design of Experiment (DOE) toolset. Most users will run the Transducer Design Advisor on their personal computers (as seen in FIG. 4), but it can also run on Unix systems. The Transducer Design Advisor is written to be easy to use. Its user interface is similar to the familiar Windows Wizards. It includes extensive on-line help to get new users up and running quickly, and also supports quick navigation methods to help experienced users get their work done faster.

When the ultrasound simulator is used with the DOE tools, there are five text files that must be created before running any simulation. Two of these files are required by the DOE software, and three are required by the ultrasound simulator. The Transducer Design Advisor creates these files based on a series of questions that the user answers as he/she moves through the Transducer Design Advisor windows. If the user is setting up a brand new simulation, the Transducer Design Advisor will walk the user through the process of creating these files from scratch. If the user is updating some files from a previous simulation, where the user only needs to tweak a few parameters, the Transducer Design Advisor will let the user edit these files efficiently and with much less chance of error than if the user used a text editor.

The two files required by the DOE software are the File Wrapper file ("*.fileWrapper") and the I/O Template file ("*.tplt"). These files allow the ultrasound simulator to talk to analysis server 100 and to pass data from the user's Excel spreadsheet 88 to the simulation and back again. For simple analysis codes, it is quite easy to write the FileWrapper and Template files by hand, and the user may never have to modify them once they are written. For the ultrasound simulator, however, the user needs to tailor these two files for a particular simulation to be run, and the set of input and output variables that the user will use may differ greatly from simulation to simulation. This happens because the largest realistic DOE experiment that one can run has only a handful of input variables, but the ultrasound simulator itself uses several hundred input parameters. The relevant output variables will also change depending on the kind of transducer being simulated.

The three files required by the ultrasound simulator for its internal use help it to expand the DOE input variables into the full parameter set that it needs to run. These three files are the Master EXIC file ("*_master.exic"), the Variable Definition file ("*.vdf"), and the CTQ Policy file ("*.pol"). The Master EXIC file contains a prototype of the full parameter file that the simulator uses. The Variable Definition File defines how the DOE input variables map into the EXIC structure. The CTQ Policy file defines the relative weights for different CTQs at different depths, so that performance tradeoffs can be made intelligently in cases where CTQs compete with each other. These files will be described in more detail later.

The five files that the user creates are named according to a stereotyped naming pattern. The user specifies the root name for the files, minus any extension, and all the files get named using the root name plus specific filename extensions for each file. For instance, if the user picks the root name "c348", then the five files will be named "c348.fileWrapper", "c348.tplt", "c348_master.exic", "c348.vdf", and "c348.pol". The root name may be the name of a particular probe being simulated.

Once the Transducer Design Advisor has been used to create or modify these files, the ultrasound simulator can be used as a DOE analysis object.

The Transducer Design Advisor is similar to a Windows "Wizard". There are no drop-down menus or toolbar icons, just a set of buttons that the user uses to navigate through a series of windows. Each window asks the user to specify the values of a few related parameters. All of the Transducer Design Advisor windows have the same set of window navigation buttons.

Depending on whether the user is creating a new set of files from scratch or editing an existing set, and depending on the particular window the user is in at the moment, some of these buttons will be disabled (grayed out) and some will be enabled. The Back, Next and Help (?) buttons are almost always available. The Next button is used to proceed to the next window in the series when the user has finished entering values on the current window. The Back button is used to return to the window the user most recently visited, or the window before that, and so on. The Finish button (when enabled) is used to zoom to the end of the program and save the user's work if the user is editing an existing set of files and only needs to make a few changes.

If the user is editing an existing file set and the user wants to quickly move to a certain window to make changes, the GoTo . . . button can be used to select the window the user wants to jump to, instead of having to tediously click the user's way from window to window. This button is only enabled when the user is editing existing files, not when the user is creating a new set of files from scratch.

The Transducer Design Advisor preferably takes the form of a "wizard" which aids the setup of simulation and optimization details. Its purpose is to increase design productivity by eliminating the possibility of invalid parameter sets. It also encapsulates considerable knowledge of the domain of probe design. A similar wizard forms part of the DOE controller block 26 (see FIG. 1).

Figure 5:
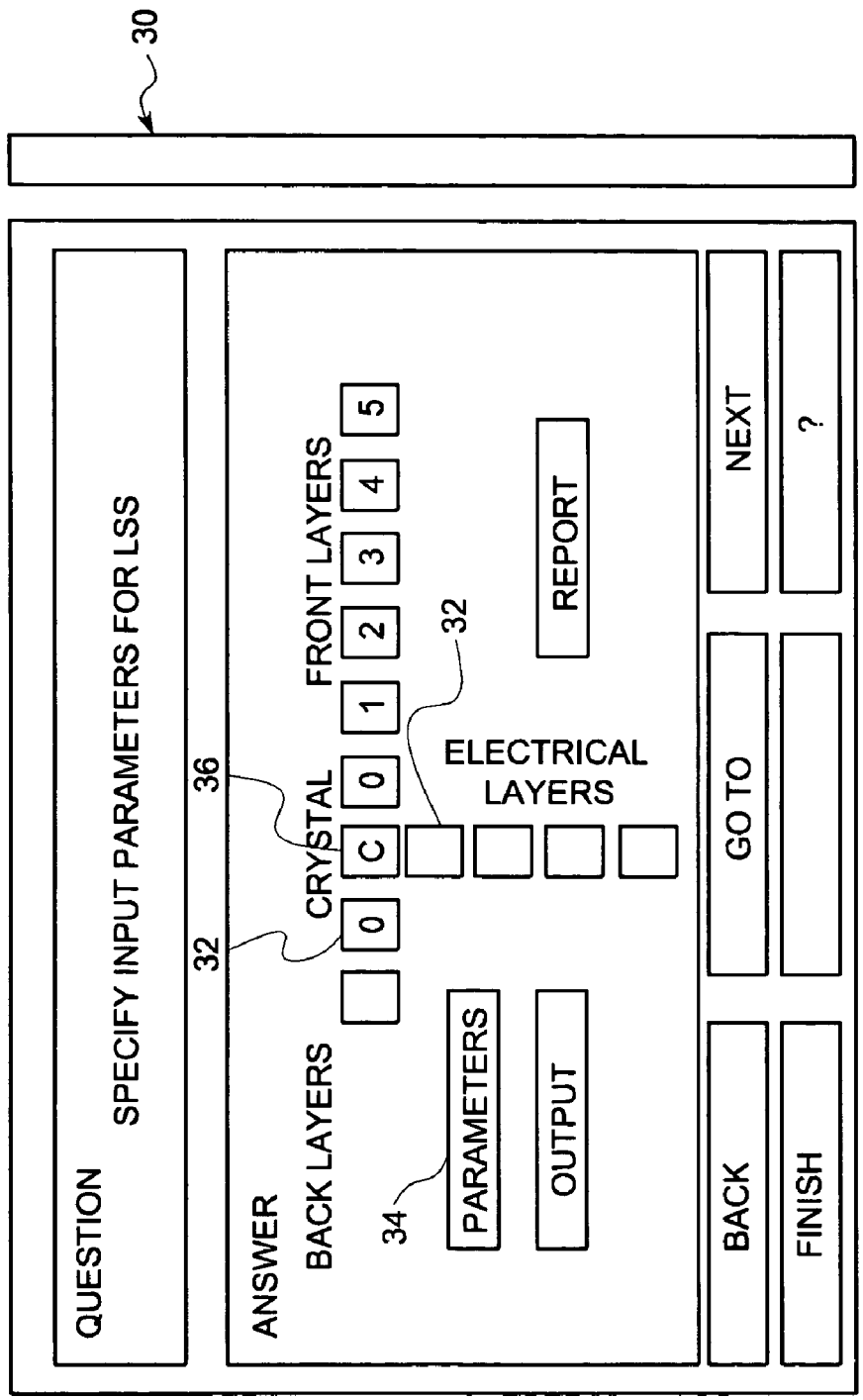
FIG. 5 is a schematic depicting a window of the Transducer Design Advisor for specifying input parameters to an acoustic stack model in accordance with the preferred embodiment of the invention.
Figure 6:
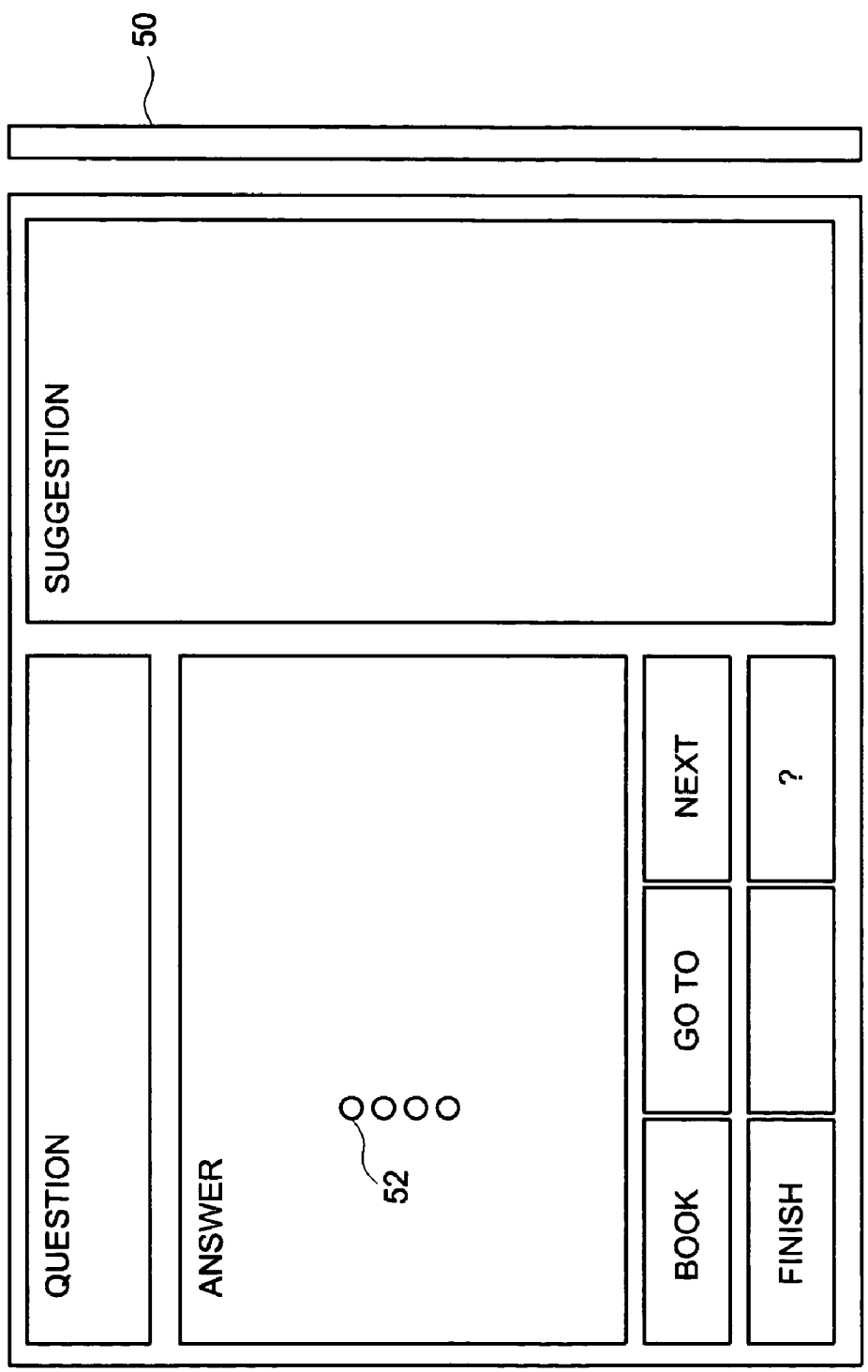
FIG. 6 is a schematic depicting a window of the Transducer Design Advisor for selecting which probe multi-row technology should be simulated in accordance with the preferred embodiment of the invention.
Figure 7:
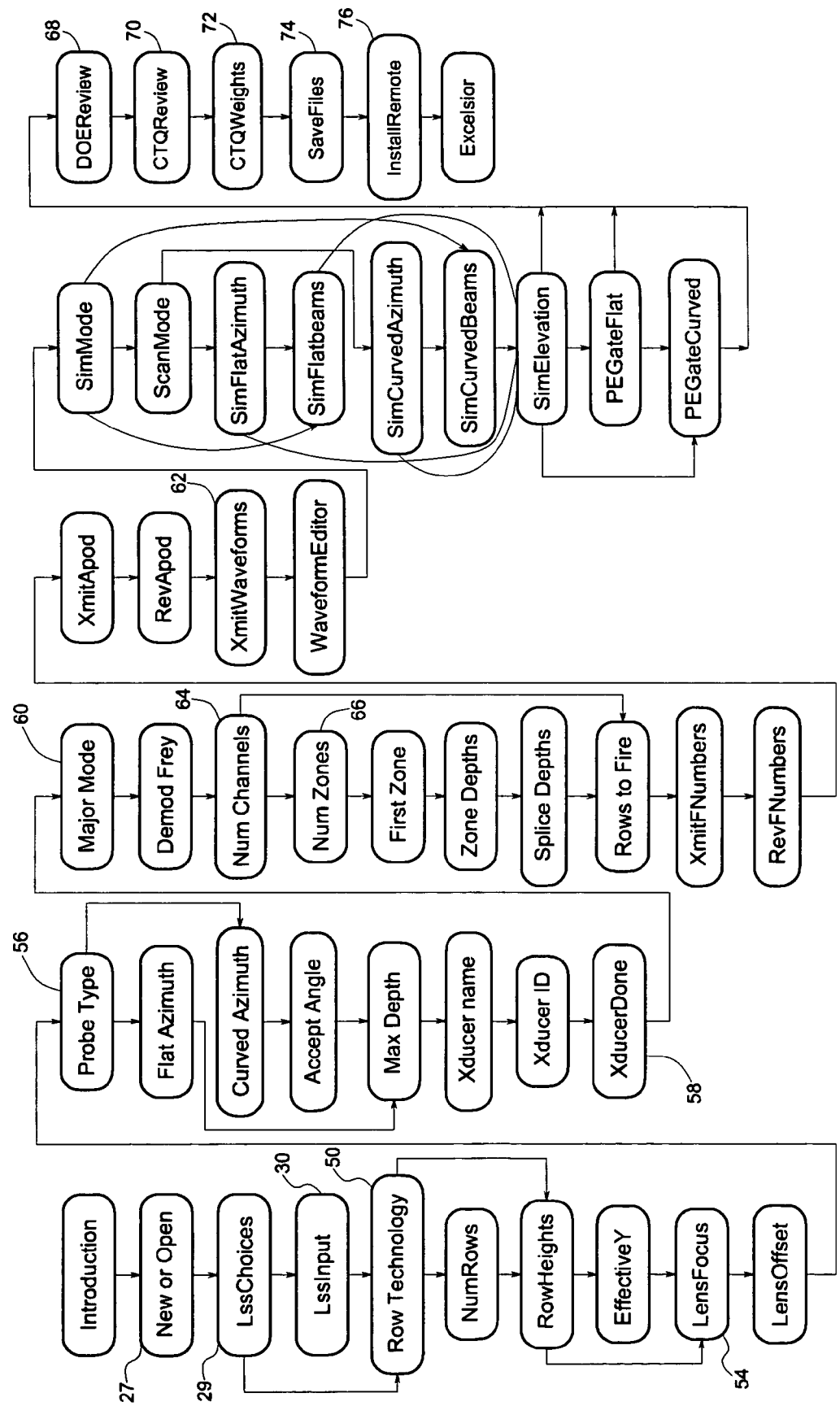
FIG. 7 is a flowchart showing the program flow for the Transducer Design Advisor in accordance with the preferred embodiment of the invention.

The Transducer Design Advisor in accordance with the preferred embodiment has about 50 different windows (three of which can be seen in FIGS. 5, 6 and 11). FIG. 7 shows an example of the flow from window to window of this wizard. The designer can move forwards and backwards through the choices until the design is ready for optimization. However, for a given transducer type, the user will only have to visit a subset of the windows. For instance, a convex probe will use a different subset of the windows than a linear probe, and a multi-row active matrix array (AMA) probe will use a different subset than a single-row probe.

The Transducer Design Advisor is implemented in Java 2. This graphical user interface is designed to be a "Wizard" similar to Windows Wizards: that is, a complicated problem is broken down into bite-sized pieces, and these pieces are presented in separate windows. The user is guided through the process one window at a time, using "Next" and "Back" buttons to navigate from one window to another. In the preferred embodiment of the Transducer Design Advisor, the "Wizard" concept was extended with several innovations: (1) In addition to "Next" and "Back" buttons, there is a "GoTo" button which the user can click to move instantly to a selected window. This button is only available when a simulation fileset is being edited; when a fileset is being created for the first time, or when major modifications are being done to an existing fileset, the "GoTo" button is not available. (2) When graphical or tabular results are being displayed, separate pop-up dialog windows are used. These windows are not part of the normal "Wizard" flow of control; instead, they are short detours from the main path. (3) The navigation paths from window to window vary depending on the user's inputs in previous windows. A central navigation database is implemented in a WindowNavigator object to control this flow of control. A small window navigation language was designed so that this database is compact but easy to maintain. During program maintenance, it is very easy to change the flow of control should additional windows be added or deleted, or should the navigation logic be changed. Changing the set of successor windows to a particular window does not require the source code for any of the windows to be changed; only the navigation database need be modified. The same database is used to support the "GoTo" button.

The Java source files that make up the Transducer Design Advisor application can be grouped into several broad categories, including top-level objects (the core objects that make up TDA windows, the central window navigation logic, and state maintenance); acoustic stack simulator objects (objects to support the 1D transducer model); animation objects (objects which support mouse-driven graphical animation); graphics objects (objects supporting line graphs, bar graphs, contour graphs and so on); phantom objects (objects supporting creating and editing phantoms for imaging); and window objects (one for every TDA window).

Figure 10:
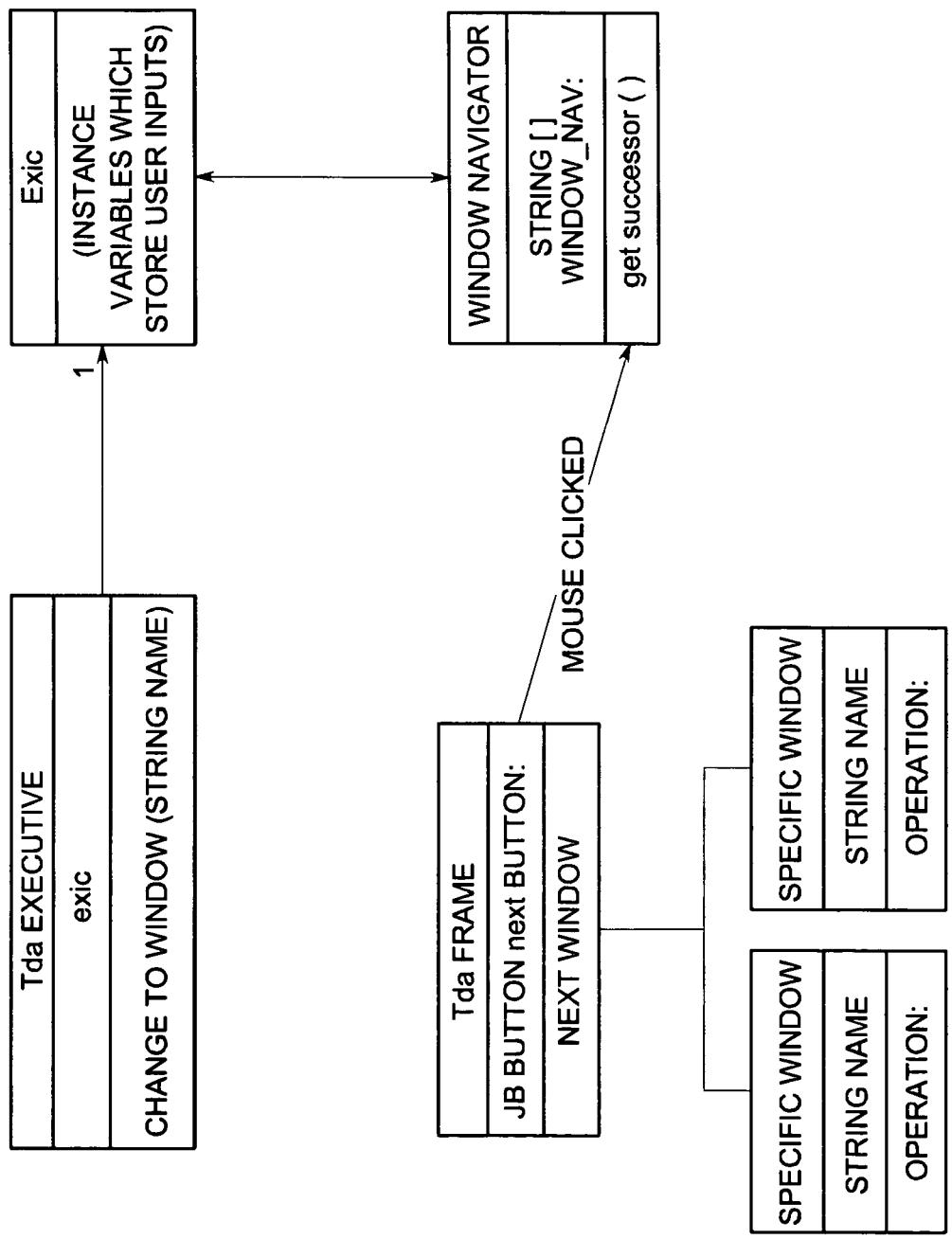
FIG. 10 is a diagram showing the class decomposition of the classes that implement the window navigation strategy of the Transducer Design Advisor in accordance with the preferred embodiment of the invention.

Referring to FIG. 10, the Main class (containing the main( ) method) in the Transducer Design Advisor is TdaExecutive. The main( ) method bootstraps the singleton instance of TdaExecutive, which creates the first window. All regular windows (not counting pop-up dialogs, help windows, and graphical output dialogs) are subclassed from TdaFrame. TdaExecutive also creates a public singleton instance of Exic. Exic is the wrapper object for an EXIC parameter file. In the Transducer Design Advisor, all state information which is in response to user inputs and which must persist from window to window, and across program invocations, is stored in the Exic object. When the user presses the Next button in a window, TdaFrame calls the getSuccessor( ) method of the singleton WindowNavigator object, which is also created by TdaExecutive. This method examines various public parameters in the Exic object to decide which of the (possibly several) successor windows to the current window should be chosen, and returns the name of the chosen window to TdaFrame. The TdaFrame then calls the changeToWindow( ) method of TdaExecutive.

A number of the windows in the Transducer Design Advisor allow the user to use the mouse to drag graphical objects in order to set some value. One example is in the wCTQWeights window (shown in FIG. 11), where the user can specify the relative weights for different CTQs by dragging nodes in a profile curve up and down. Another example is in the azimuthal simulation set-up windows. Here, the user can drag a red line indicating the beam position (for linear probes) or beam angle (for curved and sector probes). An alphanumeric readout shows the numerical value of the beam angle or position and is continually updated as the user drags the line around. If the user types a new value into the readout text field, the line is instantly updated to reflect the new value. In addition to the beam angle or position, the user can also drag the corners of a green rectangle (for linear probes) or a wedge (for curved or sector probes) to specify the minimum and maximum azimuth, and the minimum and maximum range for sampling. As with the beam, there are textual readouts that show the numerical values of these parameters, and if the text fields are updated, the graphical display is also updated.

The "sensitive" areas that will respond to mouse clicks and drags are shown on the screen. In accordance with the preferred embodiment, small square boxes are used to show the user where to click. As the user drags these boxes, their motion is constrained so that they can only move into locations that "make sense". For instance, for a curved probe, the sensitive region for specifying the beam angle is constrained to move in a circular arc.

Figure 9:
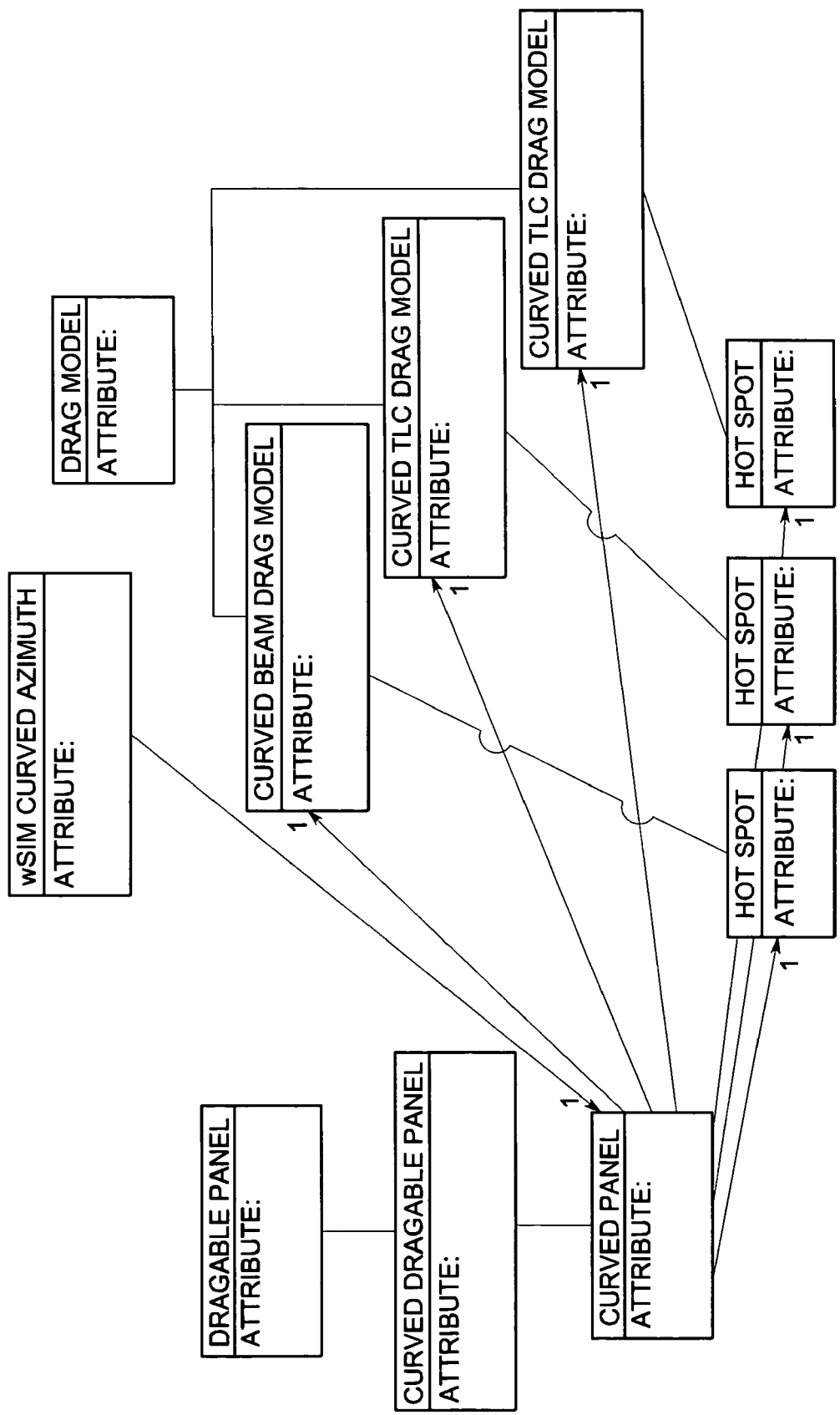
FIG. 9 is a diagram showing class decomposition of a typical window of the Transducer Design Advisor having an animated graphical display which is sensitive to mouse events in accordance with the preferred embodiment of the invention.

To support this kind of mouse-driven animation and to support useful features such as constraining the motion to a particular set of loci, a set of classes have been designed that, when subclassed, implement the animation features. Referring to FIG. 9, the DragablePanel class is a subclass of JPanel. It implements the basic "canvas" in which various dragable sensitive areas can live. A DragablePanel can support any number of sensitive areas; internally, they are organized in a Linked List. The HotSpot class is the superclass for all sensitive areas. It is basically a rectangle, which may or may not have a visual representation. A HotSpot is mainly a passive entity: the methods that cause it to be sensitive to mouse activity are in DragablePanel. A DragModel is attached to each HotSpot. The DragModel defines how the HotSpot responds to mouse motion: in particular, the DragModel implements the constraints on how (and if) the HotSpot can move in response to dragging by the mouse.

The DragablePanel, HotSpot, and DragModel together are an example of the well-known Model-View-Controller object pattern.

FIG. 9 shows a typical instance of usage for these classes. The wSimCurvedAzimuth window is where the user specifies the azimuthal and range limits for a simulation. The CurvedScan object is a subclass of CurvedDragablePanel, which is itself a subclass of DragablePanel. CurvedScan owns three HotSpots: one for the beam position and two for the upper-right and lower-left corners of a sector that specifies the azimuth and range limits. Each HotSpot is associated with a respective subclass of DragModel that specifies how that HotSpot can move as the user drags the mouse.

In general, regardless of the type of transducer the user wants to simulate, the user's journey through the Transducer Design Advisor will take a similar path (shown in FIG. 7). The user starts by telling the Transducer Design Advisor whether the user wants to edit an existing set of files or whether the user is creating a new set from scratch. In either case, the user will use a file browser window interface to pick a folder that contains the files, and to pick a root name for the file set. Next, the user specifies various geometric characteristics of the transducer, such as the number of layers in each transducer element (see FIG. 5), which multi-row technology to use (see FIG. 6), the number of rows of elements, the transducer's elevational and azimuthal size, the number of elements per row, and so on. Next, the user specifies how the user wants to simulate the imager system, picking parameters such as the major system mode to simulate (BMode, Color Flow, or PE Doppler), the azimuthal and elevation planes that the user wants to sample in the simulation, the excitation waveform to use, and so on. Finally, the user specifies weights for the various CTQs at different depths (see FIG. 11). These weights will be included in the aforementioned CTQ Policy file.

In the window for opening existing or creating new files (indicated by the block 27 in FIG. 7), the user must pick one of three choices: open an existing file set but save the output files under a different name; open an existing file set to edit its content in place; or create a new file set from scratch. Regardless of which one of these options the user picks, when the user clicks the Next button, the user will be presented with a standard file browser dialog box which the user uses to specify a folder and a root name for the new or existing file set. For the first two options, the user will browse to an existing file set and choose any of the files in that set. For the third option, the user browses to some folder where the user wants the output files to be written, and then enters the user's choice for the root name for the new file set. If the user chooses the first option, the user will actually be presented with two file browser dialog boxes: one to specify the existing file set and one to specify the new name for the output files.

The Transducer Design Advisor supports a user interface for specifying input parameters to the acoustic stack model. Preferably, this acoustic stack model uses the Krimholtz-Leedom-Matthaei (KLM) approach to create a one-dimensional model of the acoustic and electrical layers and components of the transducer. Using this user interface, the user can view and edit any of the parameters in an acoustic stack model. The user can also designate any of the acoustic stack model parameters to be DOE input variables.

In the LssChoices window 29 (see FIG. 7), the user makes a choice which determines where the user is going to get the acoustic stack model input parameters, or whether the user wants to use the acoustic stack model at all. There are four possible choices: (1) If the Transducer Design Advisor was successful in locating an acoustic stack model input file when it opened the user's existing file set, it suggests that the user simply use the parameters it has found. (2) If the Transducer Design Advisor was not successful in locating an acoustic stack model input file, the user can choose to read in acoustic stack model parameters from a file in a different location. (3) The user can also choose to start from a blank model and fill in all the parameter values by hand. (4) The user can also choose to skip over the entire acoustic stack model input window and not use an acoustic stack model at all. The acoustic stack model input parameters are kept in a text file with a ".xdcr" filename extension. If the user is editing an existing set of the Transducer Design Advisor files, the program will look for a file whose root filename is the same as the other Transducer Design Advisor files (e.g., "c348_master.exic", "c348.tplt", etc.), and which has the ".xdcr" filename extension, e.g., "c348.xdcr". If the Transducer Design Advisor finds such a file in the same directory as the user's other files and is successful in reading the file contents into a memory object, then the Transducer Design Advisor will suggest that the user start with these parameters, which the user can edit or leave as they are. If the Transducer Design Advisor cannot locate a file in the same directory as the user's other files, or if it cannot successfully read the file contents, then it disables the first choice, and the user must pick one of the other three choices.

Starting from a completely blank model and entering all the parameters by hand will be tedious. Therefore, it is preferred that the user start with some existing acoustic stack model input model. A Samples folder is provided with the Transducer Design Advisor. The Samples folder preferably contains acoustic stack models for a sampling of different probe models and types that are in actual production for one or more commercial ultrasound imagers. Since new probe designs are often similar to existing probes, these models provide a convenient starting place to begin a new design.

Once the user has made his/her choice, the user clicks the Next button to move to the next window. Unless the user has chosen the "skip acoustic stack model" option, the user proceeds to the acoustic stack model input (Lssinputs) window 30 (shown in FIG. 5).

The acoustic stack model program implements a mostly one-dimensional model of the acoustic stack. It uses the KLM model, and allows a user-defined number of layers in front of and behind the piezoelectric crystal, as well as a user-defined number of electrical components. The acoustic stack model input window allows the user to examine and modify the parameters of any component in this model, as well as change the number of layers in the acoustic or electrical chains. In addition, the user can designate any number of parameters as DOE variables, meaning that they will be available to be used as DOE input variables, and can participate in optimization experiments along with all of the parameters which relate to aperture geometry. If the user specifies one or more acoustic stack model input parameters as DOE variables, then the acoustic stack model will be invoked on each row of the DOE matrix to recalculate the impulse response of the probe.

The acoustic stack model input window 30 gives the user a graphical view of the acoustic stack model, as seen in FIG. 5. Although the acoustic stack model program itself supports any number of layers, in this window there is only room for seven layers in the front, back and electrical parts of the model. Layers that are not used in the current model are shown with the colors dimmed out. Each rectangle 32 on the screen acts like a button, which, when left-clicked by the mouse, opens up a detail window (e.g., see FIG. 8). The large rectangle 34 labeled "Parameters . . . " in the lower left allows the user to view and edit parameters that control the overall model, instead of a specific layer. When the user clicks rectangle 34, the user will see a new window appear (not shown). The first three text items in this new window control the number of layers to the front of the crystal (toward the patient), to the back of the crystal, and in the electrical stack, respectively. To change the number of active layers, the user enters a new integer greater to or equal to zero and presses the Enter key on the user keyboard. The number of rectangles that are brightly colored and dimmed out will change accordingly.

Figure 8:
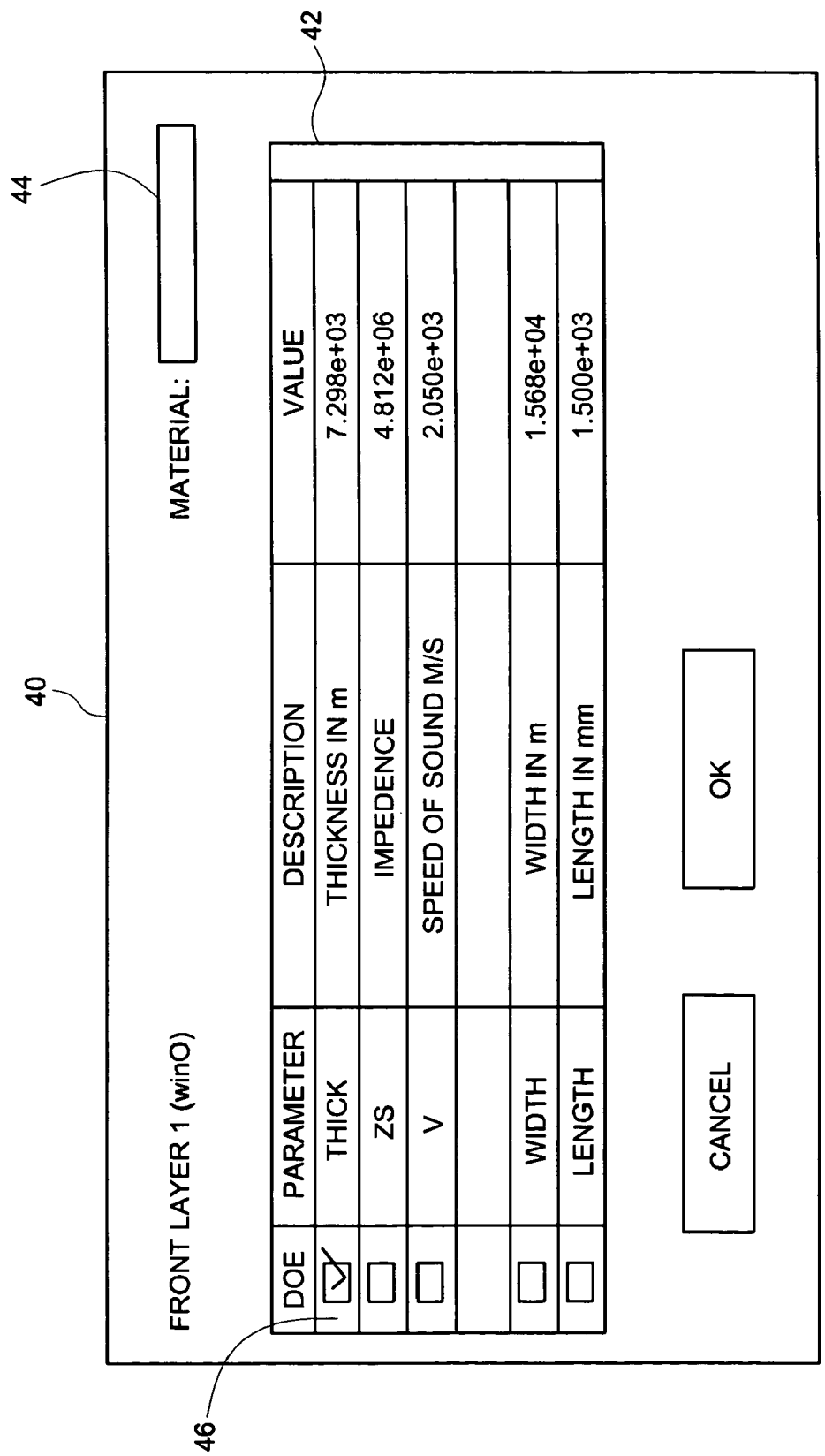
FIG. 8 is a schematic depicting a Layer Properties window of the Transducer Design Advisor which appears, in accordance with the preferred embodiment, when the user clicks on the rectangle for front layer 1 on the window shown in FIG. 3.

When the user clicks the square 36 which represents the piezoelectric crystal, or any one of the acoustic or electrical stack rectangles 32 that is not dimmed out, a Layer Properties window will appear. One such window 40, shown in FIG. 8, is produced when the box for front layer 1 (shown in FIG. 5) is clicked on. For all layers and the crystal, the same list of parameters will be shown in the Layer Properties window. However, depending on the particular role that this layer plays in the acoustic or electrical stack, various parameters will be grayed out, indicating that they are not used in this role. A button 44 appearing on the Layer Properties window provides an interface to an SQL materials properties database. Below this button is a scrolling list 42 of parameters. For each parameter, the parameter name is followed by a short descriptive string, followed by the current parameter value. The user can change the parameter value for any parameter which is not grayed out by clicking in the right-hand column (Value) and typing in a new value, followed by pressing the Enter key on the user's keyboard. The user cannot change the parameter name or description.

To the left of the parameter name is a checkbox 46. If the user clicks this checkbox, a checkmark will appear. When the user clicks this checkbox, the user is telling the Transducer Design Advisor that the user wants this parameter to become a DOE input variable. These variables will be automatically appended to the set of standard DOE input variables.

When the user is satisfied with his/her changes to the parameters for a particular layer, the user clicks the "OK" button at the bottom of the window. If the user wishes to discard any changes to the parameter values, the user clicks the "Cancel" button at the bottom left.

As seen in FIG. 7, the next window in succession is named "RowTechnology". The "RowTechnology" window 50 is shown in FIG. 6 In accordance with the preferred embodiment of the Transducer Design Advisor, any one of four different multirow technologies can be selected by clicking on a respective radio button 52. The first is just a traditional single row of elements. The second is the active matrix array (AMA) multirow technology. The third and fourth types are the 1.5D and the 1.75D probes respectively. The terms "1.5D" and "1.75D" are handy shortcuts for naming two different kinds of multirow probe. A so-called "1.5D" probe is a probe having multiple rows that span the elevation dimension of the probe, where rows at symmetrical locations in elevation are electrically tied together element by element. Such a probe can have independent focusing for elements in each distinct row, but because the elements in rows that are symmetric in elevation are tied together, the beam cannot be electrically steered in the elevation direction. A so-called "1.75D" probe has the same row geometry, but the restriction that elements in rows that are symmetrical in elevation are tied together is removed. Such a probe could be electrically steered in elevation through modest angles, but not for large angles because the number of rows, and thus sampling in elevation, is crude compared to the number of elements in the azimuth dimension, and large steering angles in elevation would produce unacceptable levels of grating lobe type artifacts in the image. All of the choices are graphically depicted on the right-hand side of the window.

As shown in FIG. 7, the Transducer Design Advisor has a multiplicity of other screens for selecting various probe geometric features and various imaging system parameters. For a multi-row probe, the user can simulate either a conventional lens or a multi-focus lens (block 54 in FIG. 7). In accordance with the preferred embodiment of the invention, the probe types which are supported in the simulator are linear (flat), convex (curved), and sector (flat). The type of probe the user chooses (block 56 in FIG. 7) will affect later questions which relate to the basic geometry of the probe.

When the user gets to the XducerDone page (58 in FIG. 7), the user has finished specifying the characteristics of the transducer being simulated, as least so far as the ultrasound simulator. The remaining windows are used to tell the ultrasound simulator how to set up the conditions under which this transducer will be simulated. Window 58 has no input parameters, and is presented to the user as a kind of progress indicator. To proceed, the user clicks on the Next button.

The ultrasound beam simulator can simulate Bmode, Color Flow, or PE Doppler. The mode is selected in the MajorMode window 60. Actually, there is really no difference between the way the simulator works in Bmode and Color Flow, but there is an important difference in PE Doppler: namely, dynamic focusing is disabled in this mode. If the user wants to simulate a probe's performance in Color Flow, the user may very well want to change things like the excitation waveform, which will typically be a longer toneburst than the short pulses used in Bmode. However, the user actually specifies the excitation waveform in a different window (the XmitWaveforms window 62 in FIG. 7) and so when the user picks Color Flow mode in this window, the user is basically just setting a flag for documentation purposes. In the XmitWaveforms window 62, the user specifies the excitation waveform to use during simulation. The user can specify a different waveform for each active focal zone. This XmitWaveforms window supports several methods for specifying the transmit waveform: the user can specify an impulse (positive one-half wave) at a particular frequency; the user can specify a toneburst of a specified number of cycles at a particular frequency; or the user can use an interactive mouse-based graphical editor to customize the transmit waveform for each zone.

For many multiplexed probes, the number of elements in the probe exceeds the number of channels in the system console. The probe multiplexer and system commutation hardware act to connect a subset of the probe elements to the available system channels to define a particular aperture, which is then often translated across the face of the probe by changing the mux state to connect a different subset of channels. The number of system channels defines the maximum transmit and receive apertures which can be used for any given mux state. In some situations, the number of system channels is the factor that limits aperture growth as the aperture expands with deeper ranges. In other situations, the aperture growth is limited by some other factor, such as element directivity or an aperture that is close to one end of the array. In any event, the ultrasound beam simulator needs to know the maximum number of system channels in order to assess the limitations on aperture growth. The Transducer Design Advisor (via the NumChannels window 64) will accept any positive number greater than or equal to 2.

For radiology, image features such as spatial resolution, contrast resolution, signal-to-noise ratio, and speckle appearance are the most important CTQs, and frame rate is much less important. For cardiology systems, frame rate is usually the most important CTQ, with the others much less important. Transmit focus is one of the most important determinants of spatial resolution. If only a single focal zone is used, then spatial resolution is good close to the transmit focus and poor everywhere else, unless a large transmit F number is used, in which case spatial resolution is poor everywhere. For this reason, radiology systems commonly employ multiple firings (zones) for each acoustic line, with the transmit focus being different for each firing, and use a small transmit F number to produce good spatial resolution for a small range close to the focus depth. The final receive data for each acoustic line is spliced together from the pieces of each receive vector which are close to the corresponding transmit focus depth for that firing. Some tapering is usually applied to avoid noticeable discontinuities in average scene brightness from zone to zone. The NumZones window 66 and several of the windows to follow ask the user to specify the number of active zones and the range of zone indices to use, and then ask the user to specify various properties on a per-zone basis.

After the user has specified the physical parameters for the transducer, and the way the user wants to set up the ultrasound beam simulator, the user is nearly finished. The next two windows (68 and 70 in FIG. 7) of the Transducer Design Advisor deal with the input and output variables that are candidates for participating in a set of simulations governed by a DOE matrix. The DOEReview window 68 allows the user to view the available DOE input variables (x's) and read descriptions of what they mean. The set of DOE variables varies somewhat depending on what kind of probe is being simulated. The subset of these variables which is applicable to the user's probe parameters will be automatically selected by the Transducer Design Advisor and displayed to the user in window 68. There are no user inputs in this window, so the user must click the Next button when the user has reviewed the input variables.

Similarly, the CTQReview window 70 (see FIG. 7) displays a list of the CTQ output variables (Y's). The list comprises a column of CTQ variable names, a column of brief descriptions of those variables, and a column indicating the units (e.g., "% change"). The units are constructed so that a positive number means a change to lower quality for that CTQ, a negative number means a change to higher quality for that CTQ, and a zero number means no change in quality for that CTQ. This is to allow an overall "Badness", or "Cost" function, to be minimized by the DOE toolset. At the beginning of a DOE simulation run, a separate simulation run (invisible to the user except for the extra time it takes) is performed to generate normalization data for computing the percentage changes. This normalization run is the same as having a row of the DOE matrix with all zeros for the encoded values. The list of CTQ output variables includes the following: ElevSLE, sidelobe energy measured in elevation; AzSLE, sidelobe energy measured in azimuth; AzMainWidth, 3 dB width of the main beam lobe measured in azimuth; ElMainWidth, 3 dB width of the main beam lobe measured in elevation; MainAx, 6 dB width of pulse measured axially; MaxInvArea, inverse of minimum azimuthal width of main lobe; MaxDiscontinuity; maximum gradient of system amplitude response over range. There are no user inputs in window 70, so the user must click the Next button to proceed.

The CTQWeights window 72 (shown in FIG. 11) allows the user to set the relative importance of each CTQ as a function of range. The value of each CTQ is an integral part of a Marketing Requirement Specification, and represents a team's collective knowledge of the clinical needs for the application(s) for a particular probe being simulated. In the computation of the overall "Badness", the CTQ values are multiplied by these weights prior to summation. This method allows for the common situation where a particular Y is crucial in a certain part of the image and less critical elsewhere. To enter a set of weights for a CTQ, where the weights vary according to range, the user simply drags a line segment up or down with the mouse pointer, with the vertical position of the line specifying the weight at each range. Each line can be broken into any number of segments with each segment specifying a different weight. A new segment boundary can be created by clicking the mouse button at the desired position with the keyboard Control key held down.

The SaveFiles window 74 (see FIG. 7) is merely a final confirmation window before the Transducer Design Advisor writes all of its output files to the folder and root name that the user originally specified. The user must click on the Next button to save the files and finish. If the user wants to first review the user's inputs for correctness, the user can use the Back button to move backwards through the windows the user has previously visited. There are two text fields in window 74: the top field shows the directory where the user's work will be saved, and the bottom field shows the root filename for all the files that will be saved.

The InstallRemote window 76 allows the user to upload the user's completed file set to the remote server 82 (see FIG. 4) which will be hosting the simulation. The "Remote Host" text field will already be filled in with the name of the preferred server for the user's installation. In order for the user to be able to upload files, the user must have already been given a username and password for the remote system. The user enters that username and password into the text fields provided. The root name for the file set the user is working on is already entered into a corresponding text field in the window. The complete file set consists of the five previously identified files. After the user has entered his/her username and password, the user clicks on an "Install" button to upload the files from the user's PC 80 to the remote server 82 via the network 84. After the installation has successfully completed, the user can proceed to the final window by clicking the Next button.

If the user has made it to the final window, the user's work has been saved and the user is now ready to create a DOE matrix and start simulating. The user exits the Transducer Design Advisor. To perform a DOE run, the user starts up Excel (with DOE extensions). The user requests that a new simulation be run. The user must specify the remote host where the simulation files have been uploaded. This host is running a copy of the analysis server 100. The analysis server detects the incoming request and sends a list of available simulations back to the user's PC 80. This list will include the new transducer simulation that was uploaded previously. The user selects this simulation. The user then uses the DOE user interface which is embedded in the extensions to Excel to specify the size of the DOE matrix to be run and the specific kind of DOE experiment pattern to run. The user then starts the simulation. For each row of the DOE matrix, the analysis server 100 will build an input parameter file (*.in) and send it to the simulation host. It will invoke the simulator with that input file. The simulator will call an "expand" program to expand the input file into a new Master Parameter file, using the information in the Variable Definition file (*.vdf) to guide this expansion. The simulation is then run with the new Master Parameter file. At the end of the simulation, the "score" program is called to calculate the "goodness" parameter using the CTQ weights contained in the Policy file. The simulator formats the CTQs and goodness measure into a "*.out" file. The simulator then terminates. The analysis server 100 reads the "*.out" file and sends the results of that run back to Excel 88 on the user's PC 80. These last two steps are repeated for each row of the DOE matrix. When all rows have been run, the user can then use other DOE tools 90 to generate regressions, examine the quality of data, build a model, make graphics, etc.

While the invention has been described with reference to preferred embodiments, it will be understood by those skilled in the art that various changes may be made and equivalents may be substituted for elements thereof without departing from the scope of the invention. For example, the computation-intensive parts of the simulation need not be implemented on a remote server. Instead the Transducer Design Advisor, simulator, analysis server and DOE tools may be implemented on a single computer having sufficient computational power. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "computer system" is a system having one or more computers.

The invention claimed is:

1. A method of jointly optimizing a performance of a probe and imager combination in an ultrasound imaging system, comprising the steps of:
    simulating images of a phantom which would be produced by said probe and imager combination in accordance with a statistical design of experiment, a probe geometry specification, and a set of imager parameters, said statistical design of experiment allowing a subset of said imager parameters to vary; and
    quantifying a diagnostic value of each image simulated based at least in part on an image quality specification to produce simulation-based image quality data.

2. The method as recited in claim 1, wherein said probe geometry specification comprises a specification of layers in said probe, and said simulating step comprises the step of computing an impulse response based at least in part on said specification of layers in said probe.

3. The method as recited in claim 2, wherein said set of imager parameters comprises a definition of aperture geometry, and said simulating step further comprises computing acoustic diffraction based at least in part on said impulse response, said definition of aperture geometry and said phantom.

4. The method as recited in claim 1, wherein at least some of said imager parameters are retrieved from a database containing respective sets of imager parameters for pre-existing probes.

5. The method as recited in claim 2, wherein said step of computing an impulse response employs a one-dimensional acoustic stack design.

6. The method as recited in claim 2, further comprising the step of generating transfer functions based at least in part on said simulation-based image quality data.

7. The method as recited in claim 6, wherein said image quality specification is a function of at least one image quality parameter, and at least one of said transfer functions relates said image quality parameter to said subset of imager parameters.

8. The method as recited in claim 7, further comprising the step of deriving a statistical distribution of said image quality parameter as a function of at least one imager parameter of said subset using at least one of said transfer functions.

9. The method as recited in claim 6, wherein said image quality specification specifies a value representing an overall image quality, and at least one of said transfer functions relates said overall image quality value to said subset of imager parameters.

10. The method as recited in claim 1, wherein said image quality specification is a function of at least the following: an image quality parameter and a range-dependent weighting coefficient corresponding to said image quality parameter.

11. The method as recited in claim 6, further comprising the step of optimizing imager parameters of said probe and imager combination based at least in part on said transfer functions.

12. The method as recited in claim 6, further comprising the step of optimizing said specification of layers in said probe based at least in part on said transfer functions.

13. The method as recited in claim 6, further comprising the step of generating a graph representing image quality as a function of cost based at least in part on said transfer functions.

14. A computer system comprising a processor, a display monitor, an operator interface, and programming for jointly optimizing a performance of a probe and imager combination in an ultrasound imaging system, comprising:
  simulating images of a phantom which would be produced by said probe and imager combination in accordance with a statistical design of experiment selected via said operator interface, a probe geometry specification comprising at least a portion specified via said operator interface, and a set of imager parameters comprising at least one imager parameter set via said operator interface, said statistical design of experiment allowing a subset of said imager parameters to vary;
  controlling said display monitor to display said simulated images; and
  quantifying a diagnostic value of each image simulated based at least in part on an image quality specification to produce simulation-based image quality data.

15. The computer system as recited in claim 14, wherein said image quality specification comprises at least a portion selected via said operator interface.

16. The computer system as recited in claim 14, wherein said operator interface comprises a graphical user interface for selecting said statistical design of experiment.

17. The computer system as recited in claim 14, wherein said operator interface comprises a graphical user interface for setting said at least one imager parameter.

18. The computer system as recited in claim 14, wherein said operator interface comprises a graphical user interface for specifying at least said portion of said probe geometry specification.

19. The computer system as recited in claim 14, wherein said probe geometry specification comprises a specification of layers in said probe,
  and said simulating step comprises the step of computing an impulse response based at least in part on said specification of layers in said probe.

20. The computer system as recited in claim 19, wherein said set of imager parameters comprises a definition of aperture geometry, and said simulating step further comprises computing acoustic diffraction based at least in part on said impulse response, said definition of aperture geometry and said phantom.

21. The computer system as recited in claim 14, further comprising a database containing respective sets of imager parameters for pre-existing probes, wherein at least some of said imager parameters are retrieved from said database.

22. The computer system as recited in claim 19, wherein said step of computing an impulse response employs a one-dimensional acoustic stack design.

23. The computer system as recited in claim 19, further comprising programming for generating transfer functions based at least in part on said simulation-based image quality data.

24. The computer system as recited in claim 23, wherein said image quality specification is a function of at least one image quality parameter, and at least one of said transfer functions relates said image quality parameter to said subset of imager parameters.

25. The computer system as recited in claim 24, further comprising programming for deriving a statistical distribution of said image quality parameter as a function of at least one imager parameter of said subset using at least one of said transfer functions.

26. The computer system as recited in claim 23, wherein said image quality specification specifies a value representing an overall image quality, and at least one of said transfer functions relates said overall image quality value to said subset of imager parameters.

27. The computer system as recited in claim 14 wherein said image quality specification is a function of at least the following: an image quality parameter and a range-dependent weighting coefficient corresponding to said image quality parameter.

28. The computer system as recited in claim 23, further comprising programming for optimizing imager parameters of said probe and imager combination based at least in part on said transfer functions.

29. The computer system as recited in claim 23, further comprising programming for optimizing said specification of layers in said probe based at least in part on said transfer functions.

30. The computer system as recited in claim 23, further comprising programming for controlling said display monitor to display a graph representing image quality as a function of cost based at least in part on said transfer functions.

31. A computer system for jointly optimizing a performance of a probe and imager combination in an ultrasound imaging system, comprising:
  a processor;
  a display monitor;
  an operator interface;
  means for simulating images of a phantom which would be produced by said probe and imager combination in accordance with a statistical design of experiment selected via said operator interface, a probe geometry specification comprising at least a portion specified via said operator interface, and a set of imager parameters comprising at least one imager parameter set via said operator interface, said statistical design of experiment allowing a subset of said imager parameters to vary;

means for controlling said display monitor to display said simulated images; and means for quantifying a diagnostic value of each image simulated based at least in part on an image quality specification to produce simulation-based image quality data.

32. A computer system comprising first and second computers connected via a network, wherein said first computer is programmed with transducer design advisor software for generating a series of graphical user interface windows, creating files which define a design of experiment analysis based at least in part on inputs to said windows, and uploading said files to said second computer, and said second computer is programmed with simulation software for simulating images of a phantom in accordance with a design of experiment defined by said uploaded files.

33. The computer system as recited in claim 32, wherein said second computer is further programmed with file server software which handles transactions between said transducer design advisor software and said simulation software.

34. The computer system as recited in claim 32, wherein first computer is further programmed with spreadsheet software having a design of experiment toolset for creating a design of experiment matrix, and said second computer is further programmed with analysis server software which provides communications links between said simulation software and said spreadsheet software.

35. The computer system as recited in claim 32, wherein said simulation software comprises acoustic stack simulation software, ultrasound beam simulation software, and design of experiment software for performing simulations in a design of experiment mode.

36. The computer system as recited in claim 32, wherein said second computer is further programmed with scoring software which calculates an image quality value using weighting coefficients received from said first computer.

37. The computer system as recited in claim 34, wherein said second computer is further programmed with scoring software which calculates an image quality value using weighting coefficients received from said first computer, and said design of experiment toolset comprises a regression tool for generating transfer functions based at least in part on said scoring.

* * * * *